United States Patent [19]

Light et al.

[11] Patent Number: 5,001,932

[45] Date of Patent: Mar. 26, 1991

[54] ULTRASONIC SQUIRTER

[75] Inventors: Glenn M. Light; William R. Van der Veer, both of San Antonio, Tex.

[73] Assignee: General Dynamics Corporation, Fort Worth, Tex.

[21] Appl. No.: 370,239

[22] Filed: Jun. 22, 1989

[51] Int. Cl.⁵ .............................................. G01N 29/04
[52] U.S. Cl. ...................................................... 73/644
[58] Field of Search .................................. 73/642, 644

[56] References Cited

U.S. PATENT DOCUMENTS

| | | |
|---|---|---|
| 3,255,626 | 6/1966 | Van Der Veer ..................... 73/644 |
| 3,612,409 | 10/1971 | Henning . |
| 3,711,020 | 1/1973 | Zelna . |
| 3,832,889 | 9/1974 | Bauer ................................... 73/642 |
| 4,033,178 | 7/1977 | Holt et al. ............................ 73/644 |
| 4,507,969 | 4/1985 | Djordjevic et al. .................. 73/644 |
| 4,526,038 | 7/1985 | Box et al. ............................. 73/644 |
| 4,680,499 | 7/1987 | Umemura et al. ................... 73/644 |
| 4,726,231 | 2/1988 | Tretout et al. ...................... 73/644 |

Primary Examiner—John Chapman
Attorney, Agent, or Firm—James E. Bradley; Charles E. Schurman

[57] ABSTRACT

An ultrasonic squirter couples transducer emitted ultrasonic waves with a structure for ultrasonic testing. The squirter has a tubular body with an outlet on one end and an inlet spaced from the outlet for delivering a flow of liquid through the body to the outlet. The transducer mounts in the body in a position for transmitting and receiving ultrasonic waves through the liquid that passes through the outlet. A nozzle secures to the outlet for discharging the flow of liquid against the structure. A ring locates at the outlet of the body just downstream from the transducer. The ring and nozzle are of an elastomeric material containing metal oxide particles to absorb unwanted sound energy.

30 Claims, 2 Drawing Sheets

ULTRASONIC SQUIRTER

BACKGROUND OF THE INVENTION

1. Field of the Invention

This invention relates in general to devices for ultrasonically testing structures for flaws, and in particular to a nozzle assembly for discharging a stream of water onto the structure, the nozzle assembly holding a transducer for emitting and receiving ultrasonic waves.

2. Description of the Prior Art

Inspection of advanced composite structures often requires the use of ultrasonic water squirter systems. These systems usually utilize through-transmission techniques to detect delamination and other internal flaws. In a through-transmission water squirter system, a nozzle discharges a stream of water against the structure. The nozzle contains a transducer which transmits ultrasonic sound waves. A receiver will be placed on the other side of the structure to receive the sound waves. The through-transmission techniques are useful in detecting the presence of internal flaws and delaminations, but cannot provide information as to the through-wall thickness location of the flaw.

In another technique, a pulse-echo squirter system is used. In this technique, the transducer both transmits and receives the sound pulse. A pulse-echo squirter system has the capability to both detect and locate in the through-wall dimension the presence of delaminations. However, in the past, the turbulence usually generated in water squirter systems has made it difficult to conduct pulse-echo inspections. This is especially true for finding near surface defects.

Many efforts have been undertaken to develop an ultrasonic squirter system which would provide a signal-to-noise level sufficient to allow the use of pulse-echo techniques and provide an acceptable near surface resolution capability. The prior art efforts have been primarily focused upon the reduction of turbulence in the water stream. Several designs have taken the approach of using baffle plates in the water stream which are drilled with numerous small holes. The intent of this approach is to reduce the Reynolds number and thereby produce a laminar flow. Others have used devices resembling electrical heat sinks which are inserted downstream of the transducer with the intention of reducing the turbulence of the flow.

SUMMARY OF THE INVENTION

The ultrasonic squirter of this invention will allow pulse-echo techniques. The squirter has a tubular housing with an outlet on one end and an inlet spaced from the outlet. A transducer mounted in the housing transmits and receives ultrasonic waves through the liquid that passes through the outlet.

An elastomeric nozzle is secured to the outlet. This nozzle is constructed of a material that has a high ability to absorb sound waves and also has an acoustic impedance closely matching water. Preferably, the material is a silicone rubber containing ferric oxide filings. A ring is located between the base of the nozzle and the transducer. This ring is also constructed of an elastomeric material specially formed for the proper acoustic impedance and to dampen or absorb sound waves. The ring has a side wall with a portion that is exposed to the flow of fluid.

The elastomeric nozzle fits on L metal base which locates on the end of the housing. The base has a neck protruding downstream. The nozzle has a counterbore that fits frictionally over the neck to retain the nozzle with the base. In the event that the nozzle accidentally strikes part of the structure, it will easily detach from the base.

DESCRIPTION OF THE PREFERRED EMBODIMENT

Figure 1:
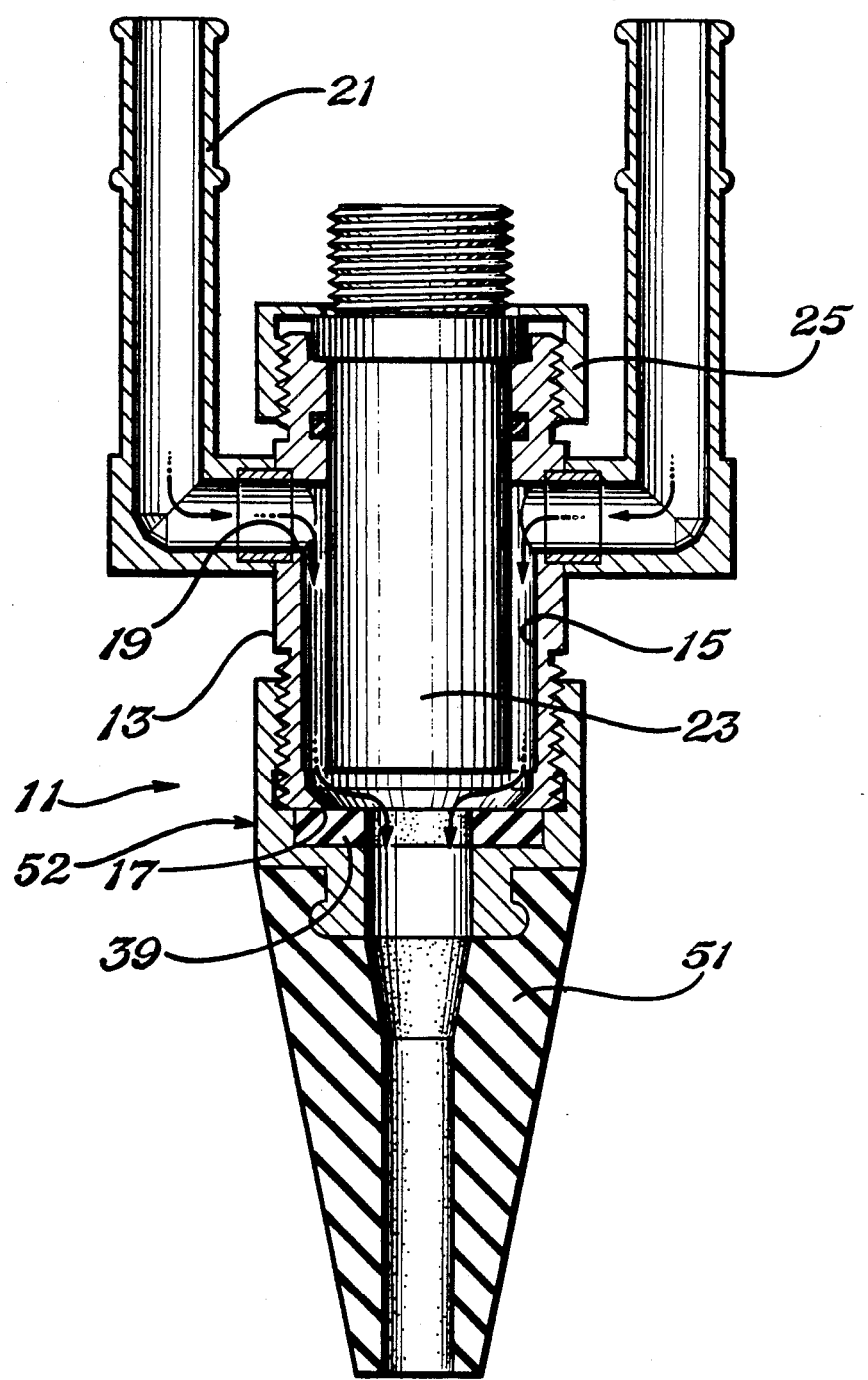
FIG. 1 is a vertical sectional view illustrating a squirter constructed in accordance with this invention.
Figure 2:
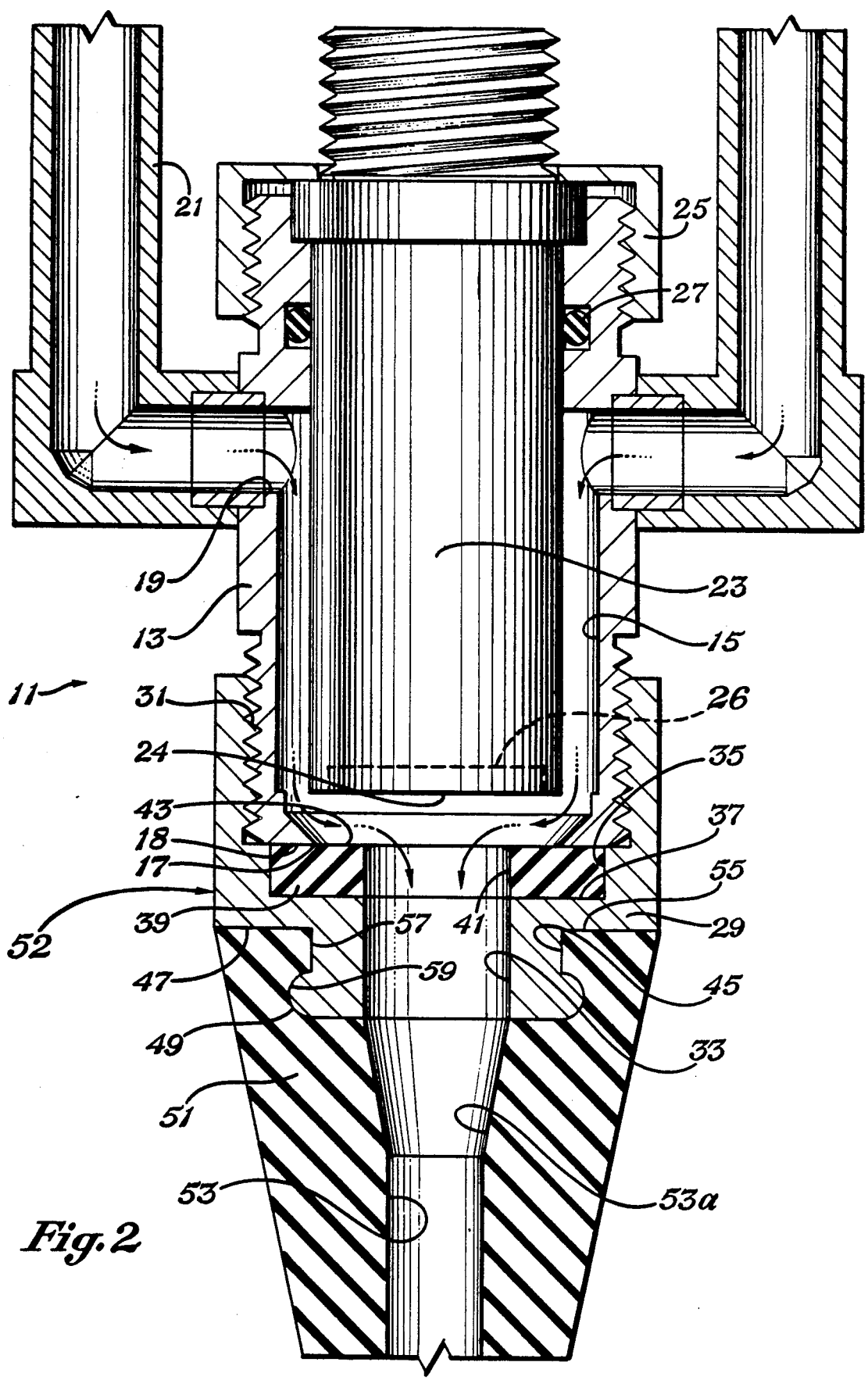
FIG. 2 is an enlarged sectional view of a portion of the squirter of FIG. 1.

Referring to FIG. 1 and FIG. 2., squirter 11 includes a tubular housing 13. Housing 13 is a generally cylindrical member, having a bore 15 extending through it. An outlet 17 locates at the downstream end of the bore 15. A rim 18 encircles the outlet 17.

Two inlets 19 are located upstream from the outlet 17. The inlets 19 enter the side wall of the housing 13 between its ends. Each inlet 19 is connected to a tube 21 which connects to a source of liquid, normally water.

A transducer 23 fits within the bore 15 of the housing 13. Transducer 23 is a conventional ultrasonic device that will both transmit ultrasonic pulses and receive ultrasonic pulses. The transducer 23 operates at various frequencies, preferably 10 megahertz (MHz). Transducer 23 is a cylindrical member having a flat downstream end 24. The downstream end 24 locates slightly upstream from the outlet 17 of the housing 13.

Transducer 23 has a piezoelectric element 26 that locates at its downstream end. Element 26 is slightly smaller in diameter than the housing of the transducer 23. Element 26 emits a sound beam which has a principal portion at the point of emission with a diameter equal to the diameter of the element 26.

The outer diameter of the transducer 23 is less than the inner diameter of bore 15 resulting in an annular clearance. As indicated by the arrows, water flows through the annular clearance and out the outlet 17. A cap 25 secures to the upstream end of the housing 13 to retain the transducer 23 in place. An 0-ring 27 seals around the outer wall of the transducer 23 to prevent leakage of water.

A base 29 secures to housing 13 on the downstream end at the outlet 17. The body of the squirter 11 includes the base 29 and the housing 13. Base 29 is a rigid member, preferably metal, which screws to the housing 13 by means of threads 31. Referring to FIG. 2, base 29 is in the preferred embodiment a metal member having a bore 33. Bore 33 is of considerably smaller diameter than the diameter of the housing bore 15. In the preferred embodiment, the diameter of the bore 33 is about one-half that of the housing bore 15.

A counterbore 35 locates at the upstream end of the bore 33. Counterbore 35 is approximately the diameter of the housing bore 15. An upstream facing annular shoulder 37 surrounds the counterbore 35. When the base 29 fully makes up to the housing 13, the base shoulder 37 will bear against the rim 18 of the housing 13.

The outlet 17 has a diameter that is smaller than the diameter of the base counterbore 35. This results in an annular cavity in the counterbore 35 A ring 39 locates in this cavity. Ring 39 is elastomeric, and is of a thickness slightly greater than the distance from the downstream side of counterbore 35 to the rim 18. Ring 39 is axially compressed in the counterbore 35. It seals liquid from the threads. The ring 39 has an outer diameter equal to the diameter of the counterbore 35. Ring 39 has an aperture 41 with a diameter that is equal to that of the base bore 33.

Ring 39 has an upstream side wall 43 that extends radially inward from the housing rim 18 a significant distance. This portion of the upstream side wall 43 will be struck by the water as it flows through the housing bore 15. The cross sectional area of the exposed portion of side wall 43 is greater than the cross sectional area of the annular space between the transducer 23 and the housing 13. Ring 39 prevents the flowing liquid from impinging directly on the base 29.

Transducer 23 emits an ultrasonic wave beam that has a principal beam diameter that increases with distance from the end 24 of transducer 23. The diameter of the side wall 43 at the periphery of the exposed portion is slightly greater than the diameter of the piezoelectric element 26. The inner diameter of aperture 41 of ring 39 is sized to be slightly larger than the principal beam diameter at the point the sound beam reaches the ring 39. The aperture diameter is sized so that the side wall 43 will intercept and attenuate "stray" sound energy without interfering with the principal beam. This stray sound is emitted from side lobes of the piezoelectric member 26.

The ring 39 thickness from the upstream side 43 to shoulder 37 is sized for the wavelength of sound in the material of the ring 39. The thickness of the ring 39 is at least two times the wavelength of sound in the material. In the preferred embodiment, the thickness is uniform and is at least three times the wavelength of sound in the material. The wavelength is calculated by dividing the velocity of sound in the material of ring 39 by the frequency of the transducer 23. The preferred material has a sound velocity of 140,000 inches per second. For a 10 MHz frequency, the wavelength will be 0.014 inch. Consequently ring 39 should have a thickness of at least 0.042 inch. In the preferred embodiment, the ring thickness was selected to be 0.125 inch.

A neck 45 protrudes from the base 29. Neck 45 is of smaller diameter than the upstream portions of base 29, resulting in a downward facing shoulder 47. A radially enlarged rim 49 forms the downstream termination of the neck 45.

A nozzle 51 attaches to the base 29. Nozzle 51, ring 39, and base 29 comprise a removable nozzle assembly 52 which secures to the housing 13 by threads 31. Nozzle 51 is of an elastomeric material and has an external conical shape. Nozzle 51 has a bore 53 that extends through it for transmitting the water pumped through the housing 13. Bore 53 has a lower portion that is slightly less in diameter than the base bore 33 and connected by a frusto-conical transition section 53a. The remaining portion of bore 53 is cylindrical. Nozzle 51 has an upward facing shoulder 55 on its upstream end. Shoulder 55 abuts against the downward facing shoulder 47 on the base 29. The inlet of nozzle bore 53 is at the junction of bore 53 with the bore 33 of the base 29.

The length of the nozzle 51 depends upon the transducer 23. The sound beam emitted by transducer 23 will have a region, known as near field, in which the waves are not uniform and are incoherent. This is a region beginning immediately with the downstream end 24. The length of the near field is equal to the diameter of transducer 23 squared divided by the wavelength of the sound energy in water at the selected frequency times four.

A far field begins at the end of the near field. The far field is uniform and linear. It diverges outward from the beam centerline at an angle equal to 1.22 times the wavelength in water at the selected frequency divided by the diameter of transducer 23. If the nozzle 51 length extends into the far field, the nozzle itself will intrude into the sound beam, thus reducing the energy transmitted into the part under test. On the other hand, the nozzle 51 length should not be so short so that the part under test is contacted by the sound beam in its near field Preferably, the maximum length of nozzle 51 is selected to be equal to the near field length of the transducer 23, and not significantly shorter than the near field length. Because the tip of the nozzle 51 is spaced at least 1½ inches from the part under test, this length of nozzle 51 will place the part under test in the far field, but not any of the nozzle 51 itself.

A counterbore 57 is formed in the upstream end of the nozzle 51. Counterbore 57 extends in a downstream direction a selected distance from the shoulder 55. Counterbore 57 has at its downstream end a radially enlarged recess 59. Recess 59 is positioned below the shoulder 55 the same distance as the rim 49 from the base shoulder 47. The recess 59 closely receives the base rim 49 to frictionally retain the nozzle 51 on the base 29.

The material of the nozzle 51 and the ring 39 is selected to have an acoustic impedance matched closely to that of the liquid flowing through the nozzle 51, normally water. The material should also have good sound absorption qualities. This reduces the reflection of ultrasonic sound waves striking this material. The preferred material is a silicone rubber containing metal particles. The metal particles both increase the density and the acoustic velocity of the elastomeric material. The particles are added in an amount needed to obtain a desired acoustic impedance. If the material does not fairly closely match that of water, increased unwanted reflection result.

The preferred metal particles are ferric oxide. Ferric oxide is a red anhydrous practical powder. It may purchased from various source. The powder is blended with the elastomeric material to achieve a substantially homogeneous mixture.

Preferably, the silicon rubber is a commercially available RTV-511 (room temperature vulcanizing) type. The desired range is 25 to 63 per cent by weight iron oxide with the remainder comprising silicon rubber. In the preferred embodiment, the ferric oxide particles comprise 37% of the nozzle 51 by weight.

The ultrasonic absorption level for the material for the transducer 23 should be at least 35 decibels. The preferred material has an absorption level of about 40 decibels. The acoustic impedance should match that of water fairly closely. Preferably the acoustic impedance differs no more than 50 per cent of the acoustic impedance of water. The acoustic impedance of the preferred material is about 172,000 grams per centimeter squared seconds. The acoustic impedance of water is less, about 148,000 grams per centimeter squared seconds.

In operation, the squirter 11 connects to a supply of water. The tip of the nozzle 51 will be placed about one and one-half inches away from the structure. Water is pumped through the tube 21, around the transducer 23 and out the outlet 17. Some turbulence of the water flow will occur at the ring 39 and in the transition section 53a. Laminar flow isn't required. The water passes through the bore 53 and strikes the structure. The flow rate of the water is fairly low, about 4 to 6 liters per minute.

The transducer 23 emits ultrasonic sound waves. The sound waves pass through the bore 53. Certain portions of the sound waves will strike the ring 39 and the side walls of the nozzle 51. This unwanted sound energy is attenuated, dampened, or absorbed by the material of the ring 39 and nozzle 51. A significant portion of the sound waves strikes the structure and reflects back through the liquid stream to the transducer end 24. Any of the portions of the sound waves striking the nozzle 51 will be absorbed to a great extent by the material of the nozzle 51.

The squirter 11 reduces unwanted reflections of the sound beam which may otherwise occur at a time very close to the reflection of the principal beam from the surface of the part being tested. This enables a very sharp pulse to be reflected back from contact with the part surface. Flaws or reflections within the part will cause a separate pulse to be reflected back which may be detected. In prior art squirters, flaws very close to the surface might not be detected because of the masking by stray reflections of the sound beam striking the surface of the part being tested.

The operator moves the squirter across the surface of the structure being tested as the testing proceeds. If the operator accidentally strikes the structure with the nozzle 51, the nozzle 51 can easily detach itself from the base 29. The nozzle 51 simply pulls loose from the neck 45 to avoid damage to the structure.

The invention has significant advantages. The ring serves to absorb unwanted ultrasonic energy. This reduces reflections back to the transducer which would cause noise and erroneous readings. The material of the ring and the nozzle serves to absorb this unwanted sound energy. Laminar flow of the water is not required. Flaws as close as 0.005 inches deep within the part from the part surface may be detected. The releasable connection of the nozzle to the nozzle base allows the nozzle to be easily detached in the event the nozzle tip strikes an object.

While the invention has been shown in only one of its forms, it should be apparent to those skilled in the art that it is not so limited, but is susceptible to various changes without departing from the scope of the invention.

We claim:

1. An ultrasonic squirter for coupling transducer emitted ultrasonic waves with a structure comprising in combination:
   a tubular body having an outlet on one end and an inlet spaced from the outlet for delivering a flow of liquid through the body to the outlet;
   means for mounting the transducer in the body in a position for transmitting ultrasonic waves through the liquid passing through the outlet;
   a nozzle secured to the body, the nozzle having a bore therethrough for discharging the flow of liquid against the structure;
   a ring located in the body, the ring having an aperture that is coaxial with the bore of the nozzle and a side wall which has at least a portion exposed to the flow of liquid through the body; and
   the nozzle and the ring being of elastomeric materials selected to absorb unwanted ultrasonic energy.

2. The squirter according to claim 1 wherein the transducer has a longitudinal axis and wherein the side wall of the ring is substantially perpendicular to said longitudinal axis.

3. The squirter according to claim 1 wherein the ring has a thickness that is substantially uniform.

4. The squirter according to claim 1 wherein the bore of the nozzle has an inlet of a selected diameter, and wherein the aperture of the ring has a diameter substantially the same as said inlet diameter.

5. The squirter according to claim 1 wherein the transducer emits ultrasonic waves having a principal beam diameter, and wherein the aperture of the ring has a diameter that is slightly larger than the principal beam diameter at the point where the beam passes through the ring.

6. The squirter according to claim 1 wherein the elastomeric material of the ring has an acoustic velocity at which sound waves travel through the elastomeric material, wherein the transducer emits ultrasonic waves at a selected frequency, the ratio of the velocity over the frequency defining a wavelength of the ultrasonic waves in the material, and wherein the ring has a thickness that is at least two times said wavelength.

7. The squirter according to claim 6 wherein the ring has a thickness that is at least three times said wavelength.

8. The squirter according to claim 1 wherein the elastomeric materials of the nozzle and the ring each has a sound attenuation of at least approximately 35 decibels and wherein each has an acoustic impedance which differs no more than approximately 50 per cent from the acoustic impedance of the liquid delivered through the body.

9. The squirter according to claim 1 wherein the transducer emits ultrasonic waves a beam having a near field of a determined length, and wherein the nozzle has a length that is substantially no greater than the length of the near field.

10. An ultrasonic squirter for ultrasonically testing a structure comprising in combination:
    a tubular body having an inner diameter and an outlet on one end;
    a transducer mounted in the body for emitting ultrasonic waves, the transducer being a cylindrical member having one end facing the outlet of the body, the transducer having a diameter less than the inner diameter of the body, defining an annular space;
    inlet means spaced from the outlet for delivering a flow of liquid through the annular space of the body to the outlet;
    a ring located in the body downstream of the annular space, the ring having an aperture and a side wall which has at least a portion exposed to the flow of liquid through the annular space;
    a nozzle secured to the body downstream of the ring, the nozzle having a bore therethrough for discharging the flow of liquid against the structure, the bore having an inlet that is of a diameter substantially equal to that of the aperture of the ring; and
    the nozzle and the ring being of elastomeric materials selected to absorb unwanted ultrasonic energy.

11. The squirter according to claim 10 wherein the elastomeric materials of the ring contain a selected amount of metal oxide particles.

12. The squirter according to claim 10 wherein the body includes a housing and a substantially rigid base secured to the housing, the nozzle being secured to the base, the housing having a rim, the base having a counterbore spaced from the rim, defining an annular cavity, and wherein the ring is located within the annular cavity.

13. The squirter according to claim 12 wherein the base has a bore downstream of the counterbore and ring and upstream of the inlet of the bore of the nozzle.

14. The squirter according to claim 10 wherein the portion of the side wall of the ring which is exposed to the flowing fluid has an area that is greater than the cross-sectional area of the annular space.

15. The squirter according to claim 10 wherein the body includes a housing and a base secured to the housing, the base having a protruding neck, the nozzle fitting frictionally over the neck, enabling the nozzle to detach from the base in the event of a lateral force being applied due to accidental contact with the structure being tested.

16. The squirter according to claim 10 wherein the transducer emits ultrasonic waves having a principal beam diameter, and wherein the aperture of the ring has a diameter that is slightly larger than the principal beam diameter at the point where the principal beam passes through the ring.

17. The squirter according to claim 10 wherein the elastomeric material of the ring has an acoustic velocity at which sound waves travel through the elastomeric material, wherein the transducer emits ultrasonic waves at a selected frequency, the ratio of the velocity over the frequency defining a wavelength of the ultrasonic waves in the material, and wherein the ring has a thickness that is at least two times said wavelength.

18. The squirter according to claim 17 wherein the ring has a thickness that is at least three times said wavelength.

19. The squirter according to claim 10 wherein the elastomeric material of the nozzle and the ring each has a sound attenuation of at least approximately 35 decibels and wherein each has an acoustic impedance which differs no more than approximately 50 per cent from the acoustic impedance of the liquid delivered through the body.

20. The squirter according to claim 10 wherein the transducer emits ultrasonic waves in a beam having a near field of a determined length, and wherein the nozzle has a length that is substantially no greater than the length of the near field.

21. An ultrasonic squirter for ultrasonically testing a structure comprising in combination:
a tubular housing having an inner diameter and an outlet on one end;
a transducer mounted in the housing for emitting ultrasonic waves, the transducer being a cylindrical member having one end facing the outlet of the housing, the transducer having a diameter less than the inner diameter of the housing, defining an annular space;
inlet means spaced from the outlet for delivering a flow of liquid through the annular space of the housing to the outlet;
a nozzle assembly having a substantially rigid tubular base, a nozzle, and a ring;
the base being secured to the housing at the outlet of the housing and having a bore therethrough which is coaxial with the outlet of the housing, the bore having an upstream end and a downstream end;
the ring being located in the base at the upstream end of the base, the ring having an aperture and a side wall which has at least a portion exposed to the flow of liquid through the annular space, the aperture being coaxial with the bore of the base;
the nozzle being secured to the base downstream of the ring, the nozzle having a bore therethrough for discharging the flow of liquid against the structure, the bore being coaxial with the bore of the base and having an inlet that is located at the downstream end of the bore of the base; and
the nozzle and the ring being of elastomeric materials selected to absorb unwanted ultrasonic energy.

22. An ultrasonic squirter for coupling transducer emitted ultrasonic waves with a structure comprising in combination;
A tubular body having an outlet on one end and an inlet spaced from the outlet for delivering a flow of liquid through the body to the outlet;
means for mounting the transducer in the body in a position for transmitting ultrasonic waves through the liquid passing through the outlet;
a nozzle secured to the body, the nozzle having a bore therethrough for discharging the flow of liquid against the structure; and
the nozzle being of an elastomeric material containing metal oxide particles for causing the material of the nozzle to absorb energy from ultrasonic waves which strike the nozzle, the elastomeric material of the nozzle having an acoustic impedance which differs no more than approximately 50 percent from the acoustic impedance of the liquid delivered through the body.

23. An ultrasonic squirter for coupling transducer emitted ultrasonic waves with a structure comprising in combination:
a tubular body having an outlet on one end and an inlet spaced from the outlet for delivering a flow of liquid through the body to the outlet;
means for mounting the transducer in the body in a position for transmitting ultrasonic waves through the liquid passing through the outlet;
a nozzle secured to the body, the nozzle having a bore therethrough for discharging the flow of liquid against the structure;
the nozzle being of an elastomeric material containing metal oxide particles for causing the material of the nozzle to absorb energy from ultrasonic waves which strike the nozzle; and
a ring located at the outlet of the body having an aperture that is coaxial with the bore of the nozzle and a side wall which has at least a portion exposed to the flow of liquid through the body, the ring being of an elastomeric material containing metal oxide particles in an amount selected to cause the material of the ring to absorb a substantial amount of any ultrasonic waves which strike the ring.

24. The squirter according to claim 22 wherein the elastomeric material of the nozzle has a sound attenuation of at least approximately 35 decibels.

25. The squirter according to claim 22 wherein the transducer emits ultrasonic waves in a beam having a near field of a determined length, and wherein the nozzle has a length that is substantially no greater than the length of the near field.

26. An ultrasonic squirter for coupling transducer emitted ultrasonic waves with a structure comprising in combination:
- a tubular body having an outlet on one end and an inlet spaced from the outlet for delivering a flow of liquid through the body to the outlet;
- means for mounting the transducer in the body in a position for transmitting ultrasonic waves through the liquid passing through the outlet;
- a nozzle secured to the body, the nozzle having a bore therethrough for discharging the flow of liquid against the structure; and
- the nozzle being of silicone rubber material containing iron oxide particles in an amount selected so that the material of the nozzle will absorb a substantial amount of any ultrasonic waves striking the nozzle, to avoid reflecting ultrasonic waves which strike the nozzle back to the transducer, the elastomeric material of the nozzle having an acoustic impedance which differs no more than approximately 50 percent from the acoustic impedance of the liquid delivered through the body.

27. The squirter according to claim 26 wherein the silicone rubber comprises substantially 25-63 per cent of the material of the nozzle, by weight, and wherein the iron oxide particles comprise substantially the remainder.

28. The squirter according to claim 26 wherein the silicone rubber comprises substantially 63 per cent of the material of the nozzle, by weight, and wherein the iron oxide particles comprise substantially the remainder.

29. The squirter according to claim 26 wherein the elastomeric material of the nozzle has a sound attenuation of at least approximately 35 decibels.

30. The squirter according to claim 26 wherein the transducer emits ultrasonic waves in a beam having a near field of a determined length and wherein the nozzle has a length that is substantially no greater than the length of the near field.

* * * * *